(12) United States Patent
Meidler et al.

(10) Patent No.: US 10,479,987 B2
(45) Date of Patent: Nov. 19, 2019

(54) THROMBIN SOLUTION AND METHODS OF USE THEREOF

(71) Applicant: Omrix Biopharmaceuticals Ltd., Rehovot (IL)

(72) Inventors: Roberto Meidler, Rehovot (IL); Oleg Belyaev, Barnaul (RU); Liliana Bar, Rehovot (IL); Israel Nur, Moshav Timmorim (IL)

(73) Assignee: Omrix Biopharmaceuticals Ltd., Rehovot (IL)

( * ) Notice: Subject to any disclaimer, the term of this patent is extended or adjusted under 35 U.S.C. 154(b) by 0 days.

(21) Appl. No.: 14/935,743

(22) Filed: Nov. 9, 2015

(65) Prior Publication Data

US 2016/0060614 A1 Mar. 3, 2016

Related U.S. Application Data

(62) Division of application No. 13/783,592, filed on Mar. 4, 2013, now Pat. No. 9,212,357.

(60) Provisional application No. 61/753,542, filed on Jan. 17, 2013.

(30) Foreign Application Priority Data

Dec. 3, 2012 (IL) .......................................... 223396

(51) Int. Cl.
| | | |
|---|---|---|
| *C12N 9/96* | (2006.01) | |
| *A61K 38/48* | (2006.01) | |
| *A61K 9/19* | (2006.01) | |
| *A61K 47/26* | (2006.01) | |
| *A61K 47/42* | (2017.01) | |
| *C12N 9/74* | (2006.01) | |

(52) U.S. Cl.
CPC ................. *C12N 9/96* (2013.01); *A61K 9/19* (2013.01); *A61K 38/4833* (2013.01); *A61K 47/26* (2013.01); *A61K 47/42* (2013.01); *C12N 9/6429* (2013.01); *C12Y 304/21005* (2013.01)

(58) Field of Classification Search
CPC .............. C12Y 304/21005; C12N 9/96; C12N 9/6429; A61K 9/19; A61K 38/4833; A61K 47/26; A61K 47/42
USPC ....................................................... 435/188
See application file for complete search history.

(56) References Cited

U.S. PATENT DOCUMENTS

| | | | |
|---|---|---|---|
| 4,877,608 | A | 10/1989 | Lee et al. |
| 5,143,838 | A | 9/1992 | Kraus et al. |
| 5,605,884 | A | 2/1997 | Lee et al. |
| 5,733,873 | A | 3/1998 | Osterberg et al. |
| 7,393,674 | B2 | 7/2008 | Jiang et al. |
| 2010/0074865 | A1 | 3/2010 | Bandyopadhyay |
| 2010/0076464 | A1* | 3/2010 | Sheetrit ............... A61L 31/10 606/151 |
| 2010/0168018 | A1 | 7/2010 | Pikal et al. |
| 2011/0045034 | A1 | 2/2011 | Nur et al. |

FOREIGN PATENT DOCUMENTS

| | | |
|---|---|---|
| CN | 101970021 | 2/2011 |
| EP | 0813598 | 6/2004 |
| EP | 1766003 | 8/2008 |
| EP | 1927658 | 10/2012 |
| JP | 63-243032 | 10/1988 |
| JP | 2-53732 | 2/1990 |
| JP | 7-165604 | 6/1995 |
| JP | 2006-117678 | 5/2006 |
| JP | 2008-503240 | 2/2008 |
| JP | 2011-513388 | 4/2011 |
| WO | WO 2007/014073 | 2/2007 |
| WO | WO 2007/029159 | 3/2007 |
| WO | WO 2011/131720 | 10/2011 |
| WO | WO 2012/020412 | 2/2012 |

OTHER PUBLICATIONS

International Preliminary Report on Patentability re: PCT/IL2013/000088 dated Jun. 9, 2015.
International Search Report re: PCT/IL2013/000088 dated May 6, 2014.
Drugs.com Evithrom, last revision Sep. 2009 available online: www.drugs.com/pro/thrombin-humna.html.
Carpenter, J.F. et al 'Rational Design of Stable Lyophilized Protein Formulations: Some Practical Advice' Pharmaceutical Research vol. 14, No. 8 (1997) pp. 969-975.
Constantino, H.R. *Lyophilization of Biopharmaceuticals* Springer (2004).
Grant Y., Engineering the rational design and optimization of lyophilization, processes for biological materials. Doctorial thesis (University, College London), 2011, pp. 23-24.
Hames, B.D. Gel electrophoresis of protein. A practical approach. 3rd addition. Oxford University Press, 1998 p. 24.
Johnson, R.E et al 'Mannitol—Sucrose Mixtures—Versatile Formulations for Protein Lyophilization' Journal of Pharmaceutical Sciences (2002) 91(4) pp. 914-922.
Pikal M.J. et al. The secondary drying stage of freeze drying: drying kinetics as a function of temperature and chamber pressure International Journal of Pharmaceutics, 60, 203-217, 1990.
Roy R.N. et al. Buffers for the physiological pH Range: thermodynamic constants of substituted aminopropanesulfonic acids from 5 to 55oC Journal of Solution Chemistry 26 (3) (1997) pp. 309-317.
https://www.genengnews.com/gen-articles/ lyophilization-growing-withbiotechnology/ 1083, Sep. 15, 2005], Accessed date Nov. 28, 2017 7 pages.

(Continued)

*Primary Examiner* — Jennifer M. H. Tichy
(74) *Attorney, Agent, or Firm* — David R. Crichton

(57) ABSTRACT

Provided are methods for lyophilization of an aqueous thrombin solution, thrombin solutions for use in such lyophilization methods, and solid thrombin compositions produced by such methods.

9 Claims, 1 Drawing Sheet

(56) References Cited

OTHER PUBLICATIONS

Manual of Therapeutic Agents 2007, Igaku-Shoin Ltd., (2007) pp. 960-961.
Willemer, H. 'Freeze drying of pharmaceutical products' Recent Drug Formulation Technique and its Application I, Iyaku (Medicine and Drug) Journal Co., Ltd. (1983) pp. 74-77.

* cited by examiner

THROMBIN SOLUTION AND METHODS OF USE THEREOF

FIELD OF THE INVENTION

The invention relates to the field of pharmaceutical solutions, and more specifically to methods for lyophilization of an aqueous thrombin solution, thrombin solutions for use in such lyophilization methods, and solid thrombin compositions produced by such methods.

BACKGROUND OF THE INVENTION

Thrombin is a proteolytic enzyme formed from prothrombinin plasma during the clotting process.

Thrombin is widely used in clinical applications as a coagulation factor to staunch bleeding of wounds by conversion of fibrinogen to fibrin. It is a common component of surgical dressings, and has been used in combination with fibrinogen and other coagulation proteins in two-component hemostatic systems such as fibrin glues, adhesives, and sealants.

It is known to lyophilize a solution of thrombin to produce a solid thrombin composition prior to storage, in order to reduce protein degradation, wherein the solid thrombin composition may be reconstituted prior to use. Lyophilization typically refers to the process of freezing a mixture and then reducing the concentration of water e.g. by sublimation to levels which do not support biological or chemical reactions. The porous and spongy solid material resulting from the lyophilization process is referred to as a cake. It is desirable for such solid thrombin compositions to have low water content (e.g. less than about 3%), to retain structural and functional stability for long periods), preferably at room temperature, and to retain a high percentage of thrombin activity upon reconstitution as compared to the activity of thrombin in the solution prior to lyophilization.

Examples of background art thrombin solutions are described in EP 813598B1; U.S. Pat. Nos. 5,605,884; 4,877,608; US 2010/0074865; U.S. Pat. No. 5,733,873; EP 1766003; and US 2010/0168018. The background art thrombin solutions vary considerably in the number and types of excipients present, and in the concentrations of the individual excipients.

Cryoprotectants or stabilizers are commonly used in thrombin solutions to protect the thrombin from denaturation or activity loss due to freezing stress, to stabilize the protein in subsequent production steps, and to extend the shelf life. Examples of cryoprotectants include saccharides such as sucrose, lactose, and trehalose; sugar alcohols such as mannitol; and surfactants such as polyethylene glycol, TritonX-100, TWEEN-20, and TWEEN-80. Besides functioning as stabilizers, mannitol and sucrose (to a lesser degree) are also used as bulking agents which help to provide a cake having a strong physical structure. Use of bulking agents is especially important for formulation with a low solid material content (per volume).

Human Serum Albumin (HSA) is also widely used in biopharmaceutical formulations as a stabilizing and bulking agent (H. R. Constantino, M. J. Pikal: Lyophilization of Biopharmaceuticals, Springer, 2004).

EP 813598B1 discloses a simple thrombin formulation for lyophilization, containing 40 mM gluconic acid, 20 mM tri-sodium citrate and 150 mM NaCl; U.S. Pat. Nos. 5,605,884 and 4,877,608 disclose formulations containing up to 10% saccharides such as sucrose, mannitol or maltose; US 2010/0074865 discloses formulation containing 5.7% lactose, 3.1% trehalose and 0.001% TWEEN-80; and U.S. Pat. No. 5,733,873 discloses formulations including 0.001-0.025% polysorbate 80 (TWEEN-80) with or without 0.1% PEG 4000 and 2% mannitol.

Sodium chloride (NaCl) is commonly used for reducing protein precipitation and aggregation during lyophilization of biopharmaceutical formulations. However, EP 1766003 discloses that NaCl can be problematic because it lowers the glass transition temperature, thereby necessitating a low temperature of primary drying and a prolonged drying cycle time. Also, US 2010/0168018 discloses a formulation without NaCl, or with NaCl present in trace amounts.

Methods of lyophilization of such known thrombin solutions are frequently of a very long duration, which increases the cost of the process and/or result in solid thrombin compositions having a relatively high water content and/or which retain a relatively low percentage of thrombin activity upon reconstitution, as compared to the thrombin activity in the solution prior to lyophilization.

SUMMARY OF THE INVENTION

The invention, in some embodiments thereof, relates to methods for lyophilization of an aqueous thrombin solution, thrombin solutions for use in such lyophilization methods, and solid thrombin compositions produced by such methods. In some embodiments, the solutions and methods disclosed herein enable solid thrombin compositions to be prepared using lyophilization methods which are shorter than known methods for lyophilization of thrombin solutions, for example, 37% shorter, thereby increasing lyophilization capacity and cost-effectiveness.

In some embodiments, the lyophilization methods described herein result in solid thrombin compositions having a relatively low water content and/or which are highly stable at room temperature over relatively long periods of time, and/or which exhibit a high thrombin activity recovery upon reconstitution. In some embodiments, the method comprises use of an optimal aqueous thrombin formulation.

Aspects and embodiments of the invention are described in the specification hereinbelow and in the appended claims.

According to an aspect of some embodiments described herein, there is provided a method for lyophilization of an aqueous thrombin solution, the method comprising providing the aqueous thrombin solution comprising about 1 to less than about 4.6% (w/v) saccharide or sugar alcohol; at least about 0.7 to lower than about 1.75% (w/v) sodium chloride; about 0.2 to about 3% albumin; calcium chloride; and sodium acetate; and lyophilizing the aqueous thrombin solution.

In some embodiments, the presence of calcium in the aqueous thrombin solution stabilizes the thrombin structure thereby preserving its activity during lyophilization. Also, calcium is required to support thrombin-hemostatic activity. Following lyophilization of an aqueous thrombin solution, a porous and spongy solid material, referred to as a cake (also referred to herein as a solid thrombin composition) is obtained.

In some embodiments, the aqueous thrombin solution comprises about 200 to about 2000 IU/ml thrombin; about 0.3 to about 1.5% (w/v) calcium chloride; and about 0.14 to about 1% (w/v) sodium acetate.

In some embodiments, the aqueous thrombin solution comprises about 1.6 to less than about 4.6% (w/v) saccharide or sugar alcohol; about 0.7 to about 1.7% (w/v) sodium chloride; higher than about 0.2 to lower than about 3% albumin; about 0.3 to about 1.2% (w/v) calcium chloride; and about 0.14 to about 0.7% (w/v) sodium acetate.

In some embodiments, the saccharide or sugar alcohol is present at a concentration of 2% (w/v); albumin is present at a concentration of about 0.6% (w/v); sodium chloride is present at a concentration of about 0.76% (w/v); calcium chloride is present at a concentration of about 0.6% (w/v) and sodium acetate is present at a concentration of about 0.27% (w/v).

In some embodiments, the aqueous thrombin solution consists essentially of thrombin; saccharide or sugar alcohol; sodium chloride; albumin; calcium chloride; and sodium acetate.

In some embodiments, the saccharide comprises a monosaccharide (optionally selected from the group consisting of glucose, fructose, galactose, xylose and ribose) and/or disaccharide (optionally selected from the group consisting of sucrose, maltose and lactose). In some embodiments, the disaccharide comprises sucrose and/or maltose, optionally at a concentration of about 2% (w/v).

In some embodiments, the sugar alcohol comprises a monosaccharide-derived sugar alcohol, optionally selected from the group consisting of mannitol, sorbitol, and xylitol.

In some embodiments, the monosaccharide-derived sugar comprises mannitol, optionally at a concentration of about 2% (w/v).

In some embodiments, the sugar alcohol is a disaccharide-derived sugar alcohol, optionally selected from the group consisting of maltitol, isomalt, and lactitol.

In some embodiments, the aqueous thrombin solution comprises a single saccharide (either monosaccharide or disaccharide) or sugar alcohol. In some embodiments, the aqueous thrombin solution is devoid of more than one kind of saccharide or sugar alcohol. In some embodiments, the aqueous thrombin solution is devoid of at least one of polyethylene glycol and histidine.

In some embodiments, the method further comprises, prior to lyophilization, adjusting the pH of the aqueous thrombin solution to a pH in the range of about 5.5 to about 9.

In some embodiments, the height of the aqueous thrombin solution in a lyophilization vessel, as measured from the lowest point of the vessel, is no greater than about 10 mm, such as, for example, about 10 mm, about 9 mm, about 8 mm, about 7 mm, or about 6 mm. In some exemplary embodiments, the height is about 8 mm.

In some such embodiments, wherein the height of the aqueous thrombin solution is no greater than about 10 mm, the total lyophilization time is no greater than about 35 hours, such as for example, about 35 hours, about 34 hours, about 33 hours, about 32 hours, about 31 hours, about 30 hours, or about 29 hours. In some exemplary embodiments, the total lyophilization time is no greater than about 30 hours.

In some embodiments, the height of the aqueous thrombin solution in a lyophilization vessel is no greater than about 20 mm. In some embodiments, the height of the aqueous thrombin solution is in the range of about 15 to about 19 mm, such as, for example, 15 mm, 16 mm, 17 mm, 18 mm, or 19 mm. In some exemplary embodiments, the height of the aqueous thrombin solution in a lyophilization vessel is about 17 mm.

In some such embodiments, wherein the height of the aqueous thrombin solution is no greater than about 20 mm, the total lyophilization time is no greater than about 68 hours.

In some embodiments, wherein the height of the aqueous thrombin solution is no greater than about 20 mm, the total lyophilization time is shorter than that of a lyophilization cycle using a control solution of identical height in a lyophilization vessel. A "control solution" has a composition which is different than the composition described herein. The control composition can be different from the composition of the invention by comprising additional or other types of excipients and/or in the concentrations of the individual excipients.

In some embodiments, the total lyophilization time as compared to that using known prior art solutions, is reduced by about 37%.

In some embodiments, lyophilizing comprises: i) subjecting the aqueous thrombin solution to a freezing procedure to produce a frozen thrombin solution; ii) subjecting the frozen thrombin solution of step i) to a primary drying procedure; and iii) subjecting the product of step ii) to a secondary drying procedure.

In some embodiments, the freezing procedure is carried out at a freezing temperature of about −45° C. to about −55° C. In some embodiments, lypophilization is carried out on a lyophilizer shelf and the freezing procedure comprises maintaining the lyophilizer shelf at a freezing temperature (also referred to herein as a freezing soak) of about −45° C. to about −55° C., such as, for example, about −50° C.

In some embodiments, the freezing procedure is carried out at a pressure of about 1 atmosphere.

In some embodiments, wherein the height of the aqueous thrombin solution in a lyophilization vessel is no greater than about 10 mm (such as about 8 mm), the freezing temperature is maintained for no longer than about 5 hours.

In some embodiments, wherein the height of the aqueous thrombin solution in a lyophilization vessel is no greater than about 20 mm (such as 15-19 mm, for example, about 17 mm), the freezing temperature is maintained for no longer than about 6 hours.

In some embodiments, the freezing temperature, such as the temperature of the lyophilizer shelf, is reached over a period (also referred to herein as a freezing ramp) of no greater than about 2.5 hours.

In some embodiments, the primary drying procedure is carried out at about −12° C. to about −18° C. In some embodiments, the primary drying procedure comprises maintaining the lyophilizer shelf at a primary drying temperature (also referred to herein as a primary drying soak) of about −12° C. to about −18° C., such as about −12° C., about −13° C., about −14° C., about −15° C., about −16° C., about −17° C., or about −18° C., at a pressure of about 100 µBar to about 160 µBar. In some exemplary embodiments, the primary drying temperature is about −15° C.

In some embodiments, the primary drying temperature, such as the temperature of the lyophilizer shelf, is reached over a period (also referred to herein as a primary drying ramp) of about 80 to about 90 minutes.

In some embodiments, wherein the height of the aqueous thrombin solution in a lyophilization vessel is no greater than about 10 mm (such as, for example, about 8 mm), the primary drying temperature and pressure are maintained for no longer than about 13 hours, such as, for example, about 13 hours, about 12 hours, or about 11 hours.

In some embodiments, wherein the height of the aqueous thrombin solution in a lyophilization vessel is no greater than about 20 mm (such as, for example, about 15 to about 19 mm, or about 17 mm), the primary drying temperature (freezing soak) and pressure are maintained for no longer than about 31 hours.

In some embodiments, the secondary drying procedure is carried out at about 20° C. to about 30° C. In some embodiments, the secondary drying procedure comprises maintaining the lyophilizer shelf at a secondary drying temperature (also referred to herein as a secondary drying soak) of about 20° C. to about 30° C. (such as, for example, about 25° C.) and a pressure of less than about 50 µBar, such as, for example, less than about 20 µBar.

In some embodiments, the temperature of the secondary drying temperature is reached over a period (also referred to as a secondary drying ramp) of about 60 to about 90 minutes.

In some embodiments, wherein the height of the aqueous thrombin solution in a lyophilization vessel is no greater than about 10 mm (such as, for example, about 8 mm), the secondary drying temperature and pressure are maintained for no longer than about 11 hours (such as, for example, about 9.5 to about 11 hours.

In some embodiments, wherein the height of the aqueous thrombin solution in a lyophilization vessel is no greater than about 20 mm (such as about 15 to about 19 mm, for example about 17 mm), the secondary drying temperature and pressure are maintained for no longer than about 15 hours. In some such embodiments, the method further comprises, prior to the secondary drying procedure, an intermediate drying procedure, carried out at about 5 to about 15° C. In some embodiments, the secondary drying procedure comprises maintaining the lyophilizer shelf at an intermediate drying temperature (also referred to herein as an intermediate drying soak) of about 5 to about 15° C., such as, for example about 10° C. In some such embodiments, the pressure during the intermediate drying procedure is about 120 µBar. In some such embodiments, the intermediate drying temperature is maintained for no longer than about 13 hours.

In some embodiments, wherein the height of the aqueous thrombin solution in a lyophilization vessel is no greater than about 10 mm (such as, for example, about 8 mm), lyophilization on a lyophilizer shelf comprises:
a) bringing the temperature of the lyophilizer shelf to a freezing temperature of about −50° C., over a time period in the range of about 1.5 to about 2.5 hours;
b) maintaining the freezing temperature for a time period in the range of about 4 to about 6 hours;
c) increasing the temperature of the lyophilizer shelf of step b) to a primary drying temperature of about −15° C. and bringing the pressure to from about 100 to about 160 µBar, over a time period in the range of about 50 to about 90 minutes;
d) maintaining the primary drying temperature and pressure for a time period in the range of about 11 to about 13 hours;
e) increasing the temperature of the lyophilizer shelf of step d) to a secondary drying temperature of about 25° C. and decreasing the pressure to less than about 50 µBar over a time period in the range of about 60 to about 90 minutes; and
f) maintaining the secondary drying temperature and pressure of step e) for a time period in the range of about 9.5 to about 11 hours.

In some embodiments, wherein the height of the aqueous thrombin solution in a lyophilization vessel is no greater than about 20 mm (such as, about 15-19 mm, for example 17 mm), lyophilization on a lyophilizer shelf comprises:
a) bringing the temperature of the lyophilizer shelf to a freezing temperature of about −50° C., over a time period in the range of about 1.5 to about 2.5 hours;
b) maintaining the freezing temperature of step a) for a time period in the range of about 4 to about 6 hours to produce a frozen thrombin solution;
c) increasing the temperature of the lyophilizer shelf of step b) to a primary drying temperature of about −15° C. and bringing the pressure to from about 100 to about 160 µBar, over a time period in the range of about 30 to about 70 minutes;
d) maintaining the primary drying temperature and pressure for a time period in the range of about 30 to about 32 hours;
e) increasing the temperature of the lyophilizer shelf of step d) to a secondary drying temperature of about 25° C. and decreasing the pressure to less than about 50 µBar, over a time period in the range of about 40 to about 80 minutes; and
f) maintaining the secondary drying temperature and pressure for a time period in the range of about 13 to about 17 hours.

In some embodiments, steps a) and b) are carried out at atmospheric pressure.

In some embodiments, there is provided a solid thrombin composition obtainable according to any of the methods described herein.

In some embodiments, the solid thrombin composition has a water content of not more than about 3% (w/w) and a thrombin activity recovery of at least 95%.

In some embodiments, the solid thrombin composition has a water content of not more than about 1.5% (w/w) and a thrombin activity recovery of at least 98%.

In some embodiments, the solid thrombin composition is stable for at least 2 years under non-freezing storage conditions, such as at room temperature.

In some embodiments, the solid thrombin composition comprises about 19.5% to about 78% (w/w of total composition) mannitol, about 1% to about 20% (w/w of total composition) sodium acetate; about 2% to about 53% (w/w of total composition) albumin; about 2.5% to about 31% (w/w of total composition) calcium chloride; and about 6% to about 45% (w/w total composition) sodium chloride.

In some embodiments, the solid thrombin composition comprises about 22% to about 66% (w/w of total composition) mannitol, about 1.5% to about 10% (w/w of total composition) sodium acetate; about 2.5% to about 43% (w/w of total composition) albumin; about 4% to about 17% (w/w of total composition) calcium chloride; and about 9.5% to about 25% (w/w of total composition) sodium chloride.

According to an aspect of some embodiments described herein, there is provided an aqueous thrombin solution comprising about 1 to less than about 4.6% (w/v) saccharide or sugar alcohol; at least about 0.7 to lower than about 1.75% (w/v) sodium chloride; about 0.2 to about 3% (w/v) albumin; calcium chloride; and sodium acetate.

In some embodiments, the aqueous thrombin solution comprises about 200 to about 2000 IU/ml thrombin; about 0.3 to about 1.5% (w/v) calcium chloride; and about 0.14 to about 1% (w/v) sodium acetate.

In some embodiments, the aqueous thrombin solution comprises about 1.6 to less than about 4.6% (w/v) saccharide or sugar alcohol; about 0.7 to about 1.7% (w/v) sodium chloride; higher than about 0.2 to lower than about 3% albumin; about 0.3 to about 1.2% (w/v) calcium chloride; and about 0.14 to about 0.7% (w/v) sodium acetate.

In some embodiments of the aqueous thrombin solution, the saccharide or sugar alcohol is present at a concentration of about 2% (w/v); the albumin is present at a concentration of about 0.6% (w/v), the sodium chloride is present at a concentration of about 0.76% (w/v), the calcium chloride is present at a concentration of about 0.6% (w/v) and the sodium acetate is present at a concentration of about 0.27% (w/v).

In some embodiments, the aqueous thrombin solution consists essentially of thrombin; saccharide or sugar alcohol; sodium chloride; albumin; calcium chloride; and sodium acetate.

In some embodiments, the saccharide is a monosaccharide, such as a monosaccharide selected from the group consisting of glucose, fructose, galactose, xylose and ribose.

In some embodiments, the saccharide is a disaccharide, such as a disaccharide selected from the group consisting of sucrose, maltose and lactose.

In some embodiments, the sugar alcohol comprises a monosaccharide-derived sugar alcohol, such as a monosaccharide-derived sugar alcohol is selected from the group consisting of mannitol, sorbitol, and xylitol. In some embodiments, the monosaccharide-derived sugar alcohol comprises mannitol, optionally at a concentration of about 2% (w/v).

In some embodiments, the aqueous thrombin solution comprises a single saccharide or sugar alcohol (such as one of sucrose alone, maltose alone, or mannitol).

In some embodiments, the aqueous thrombin solution is devoid of more than one kind of saccharide or sugar alcohol.

In some embodiments, the aqueous thrombin solution is devoid of at least one of polyethylene glycol and histidine.

In some embodiments, the aqueous thrombin has a pH in the range of about 5.5 to about 9.

In some embodiments, there is provided a method for lyophilization of an aqueous thrombin solution, comprising providing an aqueous thrombin solution as described herein; and lyophilizing the aqueous thrombin solution.

In some embodiments, the height of the aqueous thrombin solution in a lyophilization vessel is no greater than about 10 mm (such as, for example, about 8 mm). In some such embodiments, a total lyophililzation time is no greater than about 35 hours.

In some embodiments, the height of the aqueous thrombin solution in a lyophilization vessel is no greater than about 20 mm (such as about 15-19 mm, for example about 17 mm). In some such embodiments, a total lyophililzation time is no greater than about 68 hours.

In some embodiments, lyophilization comprises: i) subjecting the aqueous thrombin solution to a freezing procedure to produce a frozen protein solution; ii) subjecting the frozen thrombin solution of step i) to a primary drying procedure; and iii) subjecting the product of step ii) to a secondary drying procedure.

In some embodiments, the freezing procedure is carried out at a freezing temperature of about −45° C. to about −55° C.

In some embodiments, lyophilization is carried out on a lyophilization shelf and the freezing procedure comprises maintaining the lyophilizer shelf at a freezing temperature of about −45° C. to about −55° C., such as, for example, about −50° C.

In some embodiments, the freezing procedure is carried out at a pressure of about 1 atmosphere.

In some embodiments, the height of the aqueous thrombin solution in a lyophilization vessel is no greater than about 10 mm (such as, for example about 8 mm). In some such embodiments, the freezing temperature is maintained for no longer than about 5 hours.

In some embodiments, the height of the aqueous thrombin solution in a lyophilization vessel is no greater than about 20 mm (such as, 15-19 mm, for example about 17 mm). In some such embodiments, the freezing temperature is maintained for no longer than about 6 hours.

In some embodiments, the temperature of the lyophilizer shelf is brought to the freezing temperature over a period of no greater than about 2.5 hours.

In some embodiments, the primary drying procedure comprises maintaining the lyophilizer shelf at a primary drying temperature of about −12° C. to about −18° C. (such as, for example, about −15° C.) at a pressure of about 100 µBar to about 160 µBar.

In some embodiments, the temperature of the lyophilizer shelf is brought to the primary drying temperature over a period (also referred to herein as a primary drying ramp) of about 80 to about 90 minutes.

In some embodiments, wherein the height of the aqueous thrombin solution in a lyophilization vessel is no greater than about 10 mm (such as, for example, about 8 mm), the primary drying temperature and pressure are maintained for no longer than about 13 hours (such as, for example, about 11 to about 13 hours).

In some embodiments, wherein the height of the aqueous thrombin solution in a lyophilization vessel is no greater than about 20 mm (such as about 15 to about 19 mm, for example, about 17 mm), the primary drying temperature and pressure are maintained for no longer than about 31 hours.

In some embodiments, the secondary drying procedure comprises maintaining the lyophilizer shelf of step ii) at a secondary drying temperature of about 20° C. to about 30° C. at a pressure of less than about 50 µBar (such as, for example, less than about 20 µBar).

In some embodiments, the temperature of the lyophilizer shelf is brought to the secondary drying temperature over a period of about 60 to about 90 minutes In some embodiments, wherein the height of the aqueous thrombin solution in a lyophilization vessel is no greater than about 10 mm (such as, for example, about 8 mm), the secondary drying temperature and pressure are maintained for no longer than about 11 hours (such as, for example, about 9.5 to about 11 hours).

In some embodiments, wherein the height of the aqueous thrombin solution in a lyophilization vessel is no greater than about 20 mm (such as, about 15 to about 19 mm, for example, about 17 mm), the secondary drying temperature and pressure are maintained for no longer than about 15 hours (such as, for example, about 11 to about 13 hours). In some such embodiments, prior to step iii), the lyophilizer shelf of step ii) is maintained at an intermediate drying temperature of about 5 to about 15° C. (such as, for example, about 10° C.).

In some embodiments, the lyophilizer shelf of step ii) is maintained at the intermediate drying temperature at a pressure of 120 µBar, In some embodiments, the intermediate drying temperature is maintained for no longer than about 13 hours.

In some embodiments, wherein the height of the aqueous thrombin solution in a lyophilization vessel is no greater than about 10 mm (such as, for example, about 8 mm), lyophilization on a lyophilizer shelf comprises:
 a) bringing the temperature of the lyophilizer shelf to a freezing temperature of about −50° C., over a time period in the range of about 1.5 to about 2.5 hours;
 b) maintaining the freezing temperature of step a) for a time period in the range of about 4 to about 6 hours to produce a frozen thrombin solution;

c) increasing the temperature of the lyophilizer shelf of step b) to a primary drying temperature of about −15° C. and bringing the pressure to from about 100 to about 160 μBar, over a time period in the range of about 50 to about 90 minutes;

d) maintaining the primary drying temperature and pressure for a time period in the range of about 11 to about 13 hours;

e) increasing the temperature of the lyophilizer shelf of step d) to a secondary drying temperature of about 25° C. and decreasing the pressure to less than about 50 μBar, over a time period in the range of about 60 to about 90 minutes; and f) maintaining the secondary drying temperature and pressure for a time period in the range of about 9.5 to about 11 hours, In some embodiments, wherein the height of the aqueous thrombin solution in a lyophilization vessel is no greater than about 20 mm (such as about 15 to about 19, for example about 17 mm), lyophilization on a lyophilizer shelf comprises:

a) bringing the temperature of the lyophilizer shelf to a freezing temperature of about −50° C., over a time period in the range of about 1.5 to about 2.5 hours;

b) maintaining the freezing temperature for a time period in the range of about 4 to about 6 hours to produce a frozen thrombin solution;

c) increasing the temperature of the lyophilizer shelf of step b) to a primary drying temperature of about −15° C. and decreasing the pressure to from about 100 to about 160 μBar, over a time period in the range of about 30 to about 70 minutes;

d) maintaining the primary drying temperature and pressure for a time period in the range of about 30 to about 32 hours;

e) increasing the temperature of the lyophilizer shelf of step d) to a secondary drying temperature of about 25° C. and decreasing the pressure to less than about 50 μBar, over a time period in the range of about 40 to about 80 minutes; and f) maintaining the secondary drying temperature and pressure for a time period in the range of about 13 to about 17 hours.

In some embodiments, steps a) and b) are carried out at atmospheric pressure.

In some embodiments, there is provided a solid thrombin composition obtainable according any of the methods described herein.

In some embodiments, the solid thrombin composition has a water content of not more than about 3% (w/w) and a thrombin activity recovery of at least 95%.

In some embodiments, the thrombin composition has a water content of not more than about 1.5% (w/w) and a thrombin activity recovery of at least 98%.

In some embodiments, the solid thrombin composition is stable for at least 2 years under non-freezing storage conditions (such as at room temperature).

In some embodiments, the solid thrombin composition comprises about 19.5% to about 78% (w/w of total composition) mannitol, about 1% to about 20% (w/w of total composition) sodium acetate; about 2% to about 53% (w/w of total composition) albumin; about 2.5% to about 31% (w/w of total composition) calcium chloride; and about 6% to about 45% (w/w of total composition) sodium chloride.

In some embodiments, the solid thrombin composition comprises about 22% to about 66% (w/w of total composition) mannitol, about 1.5% to about 10% (w/w of total composition) sodium acetate; about 2.5% to about 43% (w/w of total composition) albumin; about 4% to about 17% (w/w of total composition) calcium chloride; and about 9.5% to about 25% (w/w of total composition) sodium chloride.

Unless otherwise defined, all technical and scientific terms used herein have the same meaning as commonly understood by one of ordinary skill in the art to which the invention pertains. In addition, the descriptions, materials, methods, and examples are illustrative only and not intended to be limiting. Methods and materials similar or equivalent to those described herein can be used in the practices of the present invention.

As used herein, the term "cake" or "solid cake" refers to a porous and spongy structure-like composition resulting from the lyophilization process.

As used herein, the term "collapse" with regard to a cake refers to the point at which the cake can no longer support its own structure.

As used herein, the term "solid composition" refers to a composition having a water content of equal to or less than about 3% (w/w) water such as equal to or less than 1.5%, based on the total weight of the solid composition.

As used herein, the term "thrombin activity recovery" refers to the thrombin activity in the solid composition upon reconstitution, as compared to the initial thrombin activity in the aqueous thrombin solution prior to lyophilization. Typically, the activity recovery is presented in percentage.

As used herein, the term "stable" with regard to a lyophilized/solid thrombin composition is, for example, a composition that can substantially support its own structure without collapse of the cake, and/or a composition which retains at least 80% of its activity (such as 90%, 95% or higher) for at least 2 years at non freezing temperature storage conditions e.g. at a temperature of 2-8° C. and up to room temperature such as less than 25° C. In one embodiment of the invention, the solid composition is stable for 2 years when stored at room temperature. Typically, collapse is most evidently characterized by the loss of cake structure during drying. Collapse usually results in a structure whose volume is significantly smaller than the volume of the formulation used to prepare the cake. Furthermore, a reduction of the mean pore size and porosity as well as an increase in bulk density can be observed.

The term "lyophilization" typically refers to the process of freezing a solution and then reducing the concentration of water e.g. by sublimation to levels which do not support biological or chemical reactions. The resulting lyophilized composition may be stored for a relatively long period of time. Following storage, the lyophilized composition can be used as a powder or can be reconstituted by the addition of various volumes of an aqueous solution. The volume added during reconstitution can be similar to the volume of the solution before lyophilization, lower or higher.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein the term "about" refers to ±10%.

The solutions and methods described herein enable a solid thrombin composition to be obtained by a shorter lyophilization cycle as compared to lyophilization methods currently known in the art, thereby increasing lyophilization capacity and reducing production costs. Solid thrombin compositions obtained using the solutions and methods described herein have a low water content following lyophilization, as compared to known thrombin compositions, are stable during storage at room temperature over relatively long time periods, and show a high percentage of thrombin activity recovery upon reconstitution.

BRIEF DESCRIPTION OF THE DRAWINGS

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DESCRIPTION OF SOME EMBODIMENTS OF THE INVENTION

Figure 1:
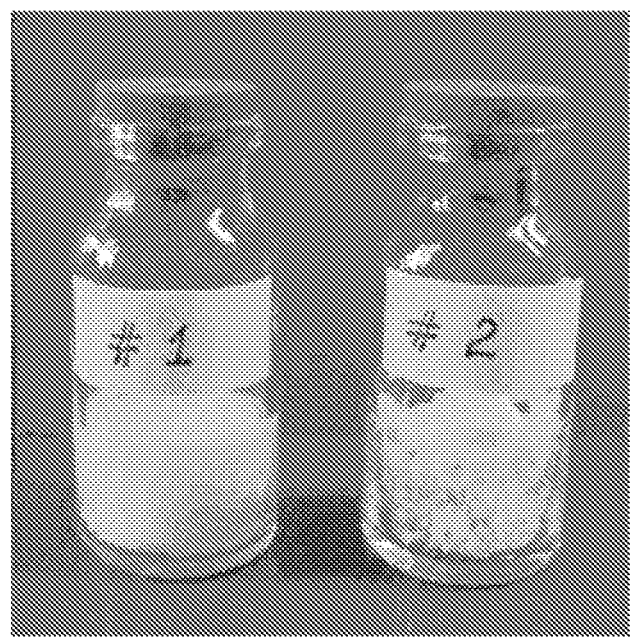
FIG. 1 shows the visual appearance of a cake obtained following an exemplary short lyophilization cycle as described herein.

The invention, in some embodiments thereof, relates to methods for lyophilization of an aqueous thrombin solution, thrombin solutions for use in such lyophilization methods, and solid thrombin compositions produced by such methods.

The principles, uses and implementations of the teachings herein may be better understood with reference to the accompanying description. Upon perusal of the description, one skilled in the art is able to implement the invention without undue effort or experimentation.

Before explaining at least one embodiment in detail, it is to be understood that the invention is not necessarily limited in its application to the details of construction and the arrangement of the components and/or methods set forth in the following description. The invention is capable of other embodiments or of being practiced or carried out in various ways. The phraseology and terminology employed herein are for descriptive purpose and should not be regarded as limiting.

As mentioned above, known thrombin solutions vary considerably in the number and types of excipients present, and in the concentrations of the individual excipients.

EXAMPLES

Materials and Methods
Thrombin Stock Solution:

The thrombin stock solution used for preparing the aqueous thrombin solutions described in the Examples below comprised about 3,500 IU/ml thrombin, about 200 mM NaCl, with stabilizers 2% mannitol and 0.2% human serum albumin (HSA) (unless indicated otherwise). The stock solution was prepared from Factor II (pro-thrombin) of human plasma that was activated and purified by sequential use of diethylaminoethyl (DEAE) cellulose anion exchange resin and SP cation exchanger resin, essentially as described in U.S. Pat. No. 5,143,838, hereby incorporated by reference.

Lyophilization:
A. Lyophilization of a Thrombin Solution of Height 8 mm within the Lyophilization Vessel:

Lyophilization was carried out on a lyophilizer shelf of a Christ Epsilon 2-8D freeze drier (Christ, Germany) in 8 ml siliconized glass vials (Schott, Germany). Each vial was filled with 2 ml aqueous thrombin solution. The height of the solution in each vial was approximately 8 mm.

Two different short lyophilization cycles were carried out as specified in Table 1 (a total time of 34 hours) and Table 2 (a total time of 30 hours) below. Temperatures given are those of the lyophilizer shelf.

Following lyophilization, a solid thrombin composition having a volume similar to the volume of the aqueous solution prior to lyophilization was obtained.

TABLE 1

| Step | Duration (hr:min) | Pressure (μbar) | Temperature (° C.) |
|---|---|---|---|
| Freezing ramp | 2 | Atm | RT to −50° C. |
| Freezing soak | 5 | Atm | −50° C. |
| Primary drying ramp | 1:30 | Atm to 140 μBar | −50° C. to −15° C. |
| Primary drying soak | 13 | 140 μBar | −15° C. |
| Secondary drying ramp | 1:30 | 140 μBar to 12 μBar | −15° C. to 25° C. |
| Secondary drying soak | 11 | 12 μBar | 25° C. |
| Total Time | 34 | | |

As used herein, the term "soak" with regard to a freezing or drying process refers to maintaining the composition being lyophilized at a constant temperature and pressure for a specified period of time in order to effect freezing or drying, respectively.

As used herein, the term "ramp" with regard to a freezing or drying process refers to a step in which the temperature and pressure of the composition being lyophilized is gradually changed over a specified period of time in order to bring the composition to a specified freezing or drying temperature and pressure respectively.

TABLE 2

| Step | Duration (hr:min) | Pressure (μbar) | Temperature (° C.) |
|---|---|---|---|
| Freezing ramp | 2 | Atm | RT to −50° C. |
| Freezing soak | 4:40 | Atm | −50° C. |
| Primary drying ramp | 1:20 | Atm to 140 μBar | −50° C. to −15° C. |
| Primary drying soak | 11 | 140 μBar | −15° C. |
| Secondary drying ramp | 1:30 | 140 μBar to 12 μBar | −15° C. to 25° C. |
| Secondary drying soak | 9:30 | 12 μBar | 25° C. |
| Total Time | 30 | | |

B. Lyophilization of a Thrombin Solution of Height 17 mm within the Lyophilization Vessel:

Lyophilization was carried out on a lyophilzer shelf of a Christ Epsilon 2-8D freeze drier (Christ, Germany) in LYOGUARD® cups (GORE®). Each vial was filled with 52 ml aqueous thrombin solution. The height of the solution in each vial was approximately 17 mm.

A short lyophilization cycles were carried out as specified in Table 3 (a total time of 68 hours). Temperatures given are those of the lyophilizer shelf.

Following lyophilization, a solid thrombin composition having a volume similar to the volume of the aqueous solution prior to lyophilization was obtained.

TABLE 3

| Step | Duration (hr:min) | Pressure (µbar) | Temperature (° C.) |
| --- | --- | --- | --- |
| Freezing ramp | 2:00 | Atm | RT to −50° C. |
| Freezing soak | 5:40 | Atm | −50° C. |
| Primary drying ramp | 0:50 | Atm to 120 µBar | −50° C. to −15° C. |
| Primary drying | 31:00 | 120 µBar | −15° C. |
| Intermediate drying ramp | 0:30 | 120 µBar | −15° C. to 10° C. |
| Intermediate drying | 12:00 | 120 µBar | 10° C. |
| Secondary drying ramp | 1:00 | 140 µBar to 12 µBar | 10° C. to 25° C. |
| Secondary drying | 15:00 | 12 µBar | 25° C. |
| Total Time | 68:00 | | |

Quantification of Water Content within the Lyophilized Thrombin Composition:

Water content determination was carried out using the volumetric Karl Fischer Titration method (KFT), which is based on the US Pharmacopoeia assay (USP 27, <921>, P. 2398-2399). Prior to the titration, the water was extracted from the lyophilized composition by adding dried methanol to the vial containing the lyophilized composition and shaking the vial. A sample from the supernatant were removed for the titration.

Determination of Thrombin Activity:

Thrombin activity of aqueous thrombin solutions was determined using a Clotting Time assay by measuring thrombin clotting activity in the different solutions according to the modified European Pharmacopeia Assay (0903/1997) procedure. Briefly, standard solutions of thrombin (4, 6, 8 and 10 IU/ml) or the test solutions were incubated for 2 minutes at 37° C. Then, 40 µl of each test solution or standard solution was mixed with 160 µl fibrinogen solution (0.1%; Enzyme research; cat No FIB1 2800L) and clotting time was measured. A calibration curve of log clotting times vs. log thrombin concentration was plotted using the standards. Thrombin activity in the different test solutions was determined by the clotting time obtained (calculated automatically by a clotting machine (Diagnostica Stago STart Coagulation Analyzer) interpolated from the calibration curve and multiplied by the dilution factor).

Thrombin Activity Recovery Following Reconstitution (% of Initial Activity):

Thrombin activity was measured as described above in the test solutions prior to lyophilization, and in the solid thrombin composition obtained by lyophilization, after reconstitution with purified water to the original volume. The recovered activity was calculated by dividing the activity obtained in the solid thrombin composition following reconstitution by the activity obtained in the thrombin solution before lyophilization and multiplying by 100.

Qualitative and Quantitative Evaluation of Solid Thrombin Compositions Obtained by a Short Lyophilization Process:

Solid thrombin compositions obtained by subjecting different aqueous thrombin solutions to a short lyophilization cycle were evaluated by the following parameters: water content of the solid compositions, thrombin activity recovery following reconstitution of the solid compositions, and structural appearance of the cake (by visual inspection). Typically, a cake having a "good structural appearance" is defined as a cake having a volume similar to that of the aqueous thrombin solution prior to lyophilization, is a monolithic block, has uniform porosity throughout the solid composition, and having no apparent wet areas.

For determining the effect of a short lyophilization process on different thrombin formulations, several aqueous thrombin solutions comprising different ingredients, e.g. different saccharides, salts, and excipients at different concentrations were prepared from the thrombin stock solution described in the "MATERIALS AND METHODS" section, and the solutions were then lyophilized using the short lyophilization cycle, as detailed in Tables 1, 2 or 3.

Example 1

Use of Different Saccharides and Concentrations or a Sugar Alcohol in a Thrombin Solution Subjected to a Short Lyophilization Cycle Disaccharides (sucrose and maltose), and a sugar alcohol (mannitol) at different concentrations were used in the preparation of aqueous thrombin solutions, and solid thrombin compositions obtained by use of such thrombin solutions in a short lyophilization cycle were studied.

Mannitol was tested at concentrations of 1.6%, 2.1%, 2.6% and 4.6% (w/v) by addition of mannitol to the diluted stock solution as described below; and sucrose and maltose were tested at a concentration of 2% (w/v). [For preparing the thrombin test solutions, the thrombin stock solution described above was diluted 1:3.5 with a solution providing the following final compositions: 0.6% human serum albumin, 20 mM sodium acetate (0.27%), 130 mM NaCl (0.76%) and 0.6% $CaCl_2$ in water at pH 7.0, and the tested saccharide or sugar alcohol was added to the solution in the concentrations listed above. In the case of mannitol, the solution was supplemented to the listed concentration (following dilution of the stock, the solution comprised about 0.6% mannitol).

Of note, human serum albumin present in the thrombin stock solution was also present in all test solutions as a "background ingredient" in a concentration of approx. 0.06%. Also, the stock solution comprised 0.6% mannitol.

The prepared aqueous thrombin solutions were lyophilized using the short lyophilization cycle as described in Table 2 above, to obtain solid thrombin compositions. The water content of each solid composition, and thrombin activity recovery following reconstitution of the lyophilized composition were measured. The results are presented in Table 4 below.

TABLE 4

| Saccharide/sugar alcohol Tested | Water content in the solid composition (%) | Thrombin Activity Recovery (%) |
| --- | --- | --- |
| Sucrose 2% | 0.4 | 96 |
| Maltose 2% | 0.6 | 95 |
| Mannitol 1.6% | 0.6 | 100 |
| Mannitol 2.1% | ND | 100 |
| Mannitol 2.6% | 0.6 | 98 |
| Mannitol 4.6% | 1.7 | 100 |

The results showed that each of the tested saccharides and sugar alcohols, when present in the aqueous thrombin solution at a concentration of 2.6% or lower, resulted in solid thrombin compositions having a low water content (0.4-0.6%) following a short lyophiliztion cycle, and high thrombin activity recovery (95-100%) following reconstitution of the solid composition.

The results also showed that the aqueous thrombin solutions resulted in cakes that maintained their structure without collapse, and which had a good structural appearance as defined above.

In contrast, an aqueous thrombin solution comprising 4.6% mannitol, when subjected to a short lyophilization cycle, resulted in a shrunken cake with a higher water content of 1.7%.

These results show that an aqueous thrombin solution for use in a short lyophilization cycle advantageously comprises about 1.6% to less than about 4.6% saccharides or sugar alcohols in order to obtain a solid and stable (structurally and functionally) thrombin composition.

Example 2

Use of Different Concentrations of Human Serum Albumin in a Thrombin Solution Subjected to a Short Lyophilization Cycle Different concentrations of HSA were used in the preparation of aqueous thrombin solutions, and solid thrombin compositions obtained by use of such thrombin solutions in a short lyophilization cycle were studied.

HSA was tested at the following concentrations: 0.2%, 0.6%, 3% and 10%.

The solutions were prepared from the thrombin stock solution by 1:3.5 dilution with a solution providing the following final composition: 2.6% mannitol, 20 mM sodium acetate (0.27%), 130 mM NaCl (0.76%) and 0.6% $CaCl_2$ in water at pH 7.0.

Of note, human serum albumin was present in all test solutions at a concentration of approx. 0.06%, (in addition to the added HSA concentrations listed above).

The prepared aqueous thrombin solutions were lyophilized using the short lyophilization cycle described in Table 2 above, wherein the solution had a height of about 8 mm in the lyophilization vessel, to obtain solid thrombin compositions. The water content of each solid composition, and thrombin activity recovery following reconstitution of the solid composition were measured. The results are presented in Table 5 below.

TABLE 5

| HSA concentration (%) | Water content in the solid composition (%) | Thrombin activity recovery (%) |
|---|---|---|
| 0.2 | 3.0 | 100 |
| 0.6 | 0.6 | 98 |
| 3 | ND | 89 |
| 10 | 0.3 | 28 |

The results showed that changing the HSA concentration had a significant effect on the water content in the solid thrombin composition and on the thrombin activity recovery following reconstitution of the solid composition.

More specifically, it was shown that a thrombin solution containing 0.6% HSA resulted in a solid composition having both relatively low water content and a high recovery of thrombin activity upon reconstitution. In contrast, thrombin solutions with lower HSA concentrations resulted in solid compositions with increased water content, while solutions with higher HSA concentrations resulted in a lower recovery of thrombin activity upon reconstitution.

Therefore, it is shown that optimal thrombin solutions advantageously comprise HSA at a concentration of higher than about 0.2% to lower than about 3%.

Example 3

Use of Different Salts and Concentrations in a Thrombin Solution Subjected to a Short Lyophilization Cycle A. Effect of Sodium Chloride (NaCl) Concentration:

Different concentrations of NaCl (90 mM, 120 mM and 150 mM, i.e. 0.5% w/v, 0.7 w/v, and 0.9 w/v, respectively) were used in the preparation of aqueous solutions devoid of thrombin, and solid compositions obtained by use of such solutions in a short lyophilization cycle were studied, wherein the height of the solutions in a lyophilization vessel was about 8 mm.

The solutions contained, in addition to the different concentrations of NaCl, 2% mannitol, 0.6% HSA, 20 mM sodium acetate (0.27%), and 0.6% $CaCl_2$ at pH 7.0.

The solutions were lyophilized using a short cycle similar to that described in Table 2 above, wherein the height of the solution in the lyophilization vessel was about 8 mm, wherein the primary drying soak was an hour longer than described in Table 2.

Following lyophilization, the water content in the solid composition was tested. The results are presented in Table 6 below.

TABLE 6

| NaCl Concentration | Water content in the solid composition (%) |
|---|---|
| 90 mM/0.5% w/v | 3% |
| 120 mM/0.7% w/v | 1.2% |
| 150 mM/0.9% w/v | <1.2% |

As shown in the Table, the water content was inversely proportional to NaCl concentration up to 150 mM.

In additional similar experiments using thrombin solutions and solutions devoid of thrombin (data not shown), no further decrease in water content was found when NaCl concentration was increased beyond 150 mM.

NaCl concentrations of 300 mM (1.75% w/v) and above had an inhibitory effect on thrombin activity as measured by clotting time assay (data not shown).

With regards to structural appearance of the solid composition, a cake prepared from a solution comprising 90 mM NaCl had a poor appearance, being shrunken compared to the volume of the solution from which it was prepared, and having a granular consistency, with non-uniform porosity throughout the solid composition.

Therefore, it was concluded that advantageously optimal thrombin solutions comprise NaCl at a concentration of at least 120 mM (0.7% w/v) to lower than 300 mM (1.75% w/v).

B. Effect of Partial Replacement of NaCl by Potassium Chloride (KCl)

The potential use of KCl instead of NaCl in the thrombin solution was assessed. Since NaCl is present in the thrombin stock solution used to prepare the test solutions, it cannot be completely removed and thus the solution was supplemented with 65 mM KCl (bringing the solution to a final salt concentration of about 125 mM). Also, an additional thrombin solution was tested, comprising the stock solution supplemented with NaCl, bringing the solution to a final salt concentration of 130 mM).

Solutions supplemented with NaCl or with KCl were prepared by diluting stock solution 1:3.5, to provide a NaCl concentration of 60 mM. A first solution was then supplemented to an NaCl concentration of 130 mM; and a second solution was supplemented with 65 mM KCl.

The stock solution was diluted so as to provide the following final composition: 2.6% mannitol, 20 mM sodium acetate (0.27%), and 0.6% $CaCl_2$ in water at pH 7.0.

The prepared solutions were lyophilized using the short lyophilization cycle described in Table 2 above, wherein the solution has a height in the lyophilization vessel of about 8 mm, and the water content in the solid compositions and the thrombin activity recovery following reconstitution of the solid composition were measured. The results are presented in Table 7 below.

TABLE 7

| Salt Tested | Water content in the solid composition (%) | Thrombin activity recovery (%) |
|---|---|---|
| 130 mM NaCl (0.76% w/v) | 0.6 | 98 |
| 65 mM (0.49% w/v) KCl; and 60 mM (0.35% w/v) NaCl | 5.2 | 100 |

It was found that partial replacement of NaCl with KCl in the solution had a detrimental effect on the water content of the solid thrombin composition obtained following a short lyophilization cycle (5.2% water content of solid composition following lyophilization of a solution containing NaCl plus KCl, as compared to 0.6% following lyophliztion of a solution containing NaCl without KCl). Similar thrombin activity recovery was obtained following reconstitution of a solid composition obtained from lyophilization of a solution comprising 130 mM NaCl and a solution comprising 65 mM KCl and 60 mM NaCl, as shown in Table 7.

Visual inspection of the structural appearance of the solid composition revealed that replacement of NaCl with KCl resulted in a shrunken cake.

It was therefore concluded that advatagously in order to obtain a solid composition with a relatively low water content, it is preferred that KCl is absent from the thrombin solution.

It is further concluded that an optimal aqueous thrombin solution that yields a solid composition with low water content and a high thrombin activity recovery following lyophilization using a short cycle comprises about 1.6% to less than about 4.6% of saccharide or sugar alcohol, at least about 120 mM (0.7% w/v) to lower than about 300 mM (1.75% w/v) sodium chloride, and higher than about 0.2% to lower than about 3% albumin, in addition to about 0.3 to about 1.2% calcium chloride; and about 0.14 to about 0.7% sodium acetate.

Example 4

Use of the Solutions Described Herein and Solutions Similar to Prior Art Solutions in a Short Lyophilization Cycle with Height of Solution in Lyophilization Vessel of 8 mm Three solutions were prepared: a solution as described herein, and two solution which are similar to prior art solutions, as follows:

1. A thrombin solution as described herein, comprising 2% mannitol, 0.6% human serum albumin, 20 mM sodium acetate (0.27%), 130 mM sodium chloride (0.76%) and 40 mM $CaCl_2$ (0.6%) in distilled water at pH 7.0.
2. A thrombin solution similar to that disclosed in EP 1766003B1 (Jiang et al.), comprising 3% sucrose, 4% mannitol, 150 mM NaCl (0.9%), 0.1% polyethylene glycol 3350 (PEG3350), 4 mM $CaCl_2$ (0.04%); and 5 mM (0.08%) histidine in distilled water at pH 6.0.
3. A thrombin solution similar to that disclosed in EP 813598B1 (MacGregor et al.), comprising 40 mM (0.78%) gluconic acid, 20 mM (0.5%) tri-sodium citrate and 150 mM NaCl (0.9%) in distilled water at pH 6.5.

The components of the solutions are further presented in Table 8.

TABLE 8

| | Solution 1 | Solution 2 | Solution 3 |
|---|---|---|---|
| Mannitol | 2% | 4% | — |
| Albumin | 0.6% | — | — |
| Sodium acetate | 0.27% | — | — |
| Sodium chloride | 0.76% | 0.9% | 0.9% |
| Calcium chloride | 0.6% | 4 mM (0.04%) | — |
| Sucrose | — | 3% | — |
| PEG | — | 0.1% | — |
| Histidine | — | 5 mM (0.08%) | — |
| Gluconic acid | — | — | 40 mM (0.78%) |
| Tri-sodium citrate | — | — | 20 mM (0.5%) |

All three thrombin solutions were prepared by diluting the thrombin stock solution described above 1:3.5 with a solution comprising the ingredients listed in each solution 1-3. Mannitol and human serum albumin were present in all three test solutions in a concentration of approx. 0.6% and 0.06%, respectively, as background ingredients The solutions were lyophilized using the short lyophilization cycles described in Table 1 or Table 2 above (wherein the height of the solution in the lyophilization vessel was about 8 mm) Water content of the solid thrombin composition, and thrombin activity recovery after reconstitution of the solid thrombin composition were measured, as described above.

FIG. 1 shows the visual appearance of a solid thrombin composition obtained following a short lyophilization of the aqueous thrombin solution described herein (solution 1; #1 in FIG. 1); and a solid thrombin composition obtained following a short lyophilization of a solution according to EP 1766003B1 (solution 2; #2 in FIG. 1). The solid composition shown in FIG. 1 was obtained using the cycle as described in Table 1. Similar results were obtained when the cycle as described in Table 2 was used.

Visual inspection of the appearance of the solid thrombin compositions revealed that the solid compositions obtained following lyophilization of the thrombin solution according to the invention and of solution 3 had a "good structural appearance" according to the definition discussed above. However, the cake obtained following use of the thrombin solution according to EP 1766003B1 (solution 2) in the short lyophilization cycle had a granulated structure.

Water content in the three solid thrombin compositions and the thrombin activity recovery of the solid compositions is presented in Table 9 below.

TABLE 9

| Thrombin Solution Tested | Water Content in the solid composition (%) | | | Thrombin activity recovery (%) | | Average thrombin activity recovery (%) ±SD |
|---|---|---|---|---|---|---|
| | Cycle of Table 1 | Cycle of Table 2 | Average water content (%) ±SD | Cycle of Table 1 | Cycle of Table 2 | |
| Solution 1 | 0.8 | 0.6 | 0.7 ± 0.14 | 100 | 98 | 99 ± 1.4 |
| Solution 2 | 3.2 | 4.1 | 3.65 ± 0.64 | 92 | 96 | 94 ± 2.8 |
| Solution 3 | 1.6 | 3.3 | 2.45 ± 1.2 | 93 | 91 | 92 ± 1.4 |

As shown in Table 9, it was found that following the short lyophilization cycle (as described in Tables 1 or 2), the lowest average water content was found in the lyophilized solid composition prepared using the solution described herein (0.7±0.14%).

As further shown in Table 9, it was found that following reconstitution of the short-cycle lyophilized solid compositions, the highest thrombin activity recovery was obtained in the solid compositions prepared using the solution described herein (99±1.4%) according to Tables 1 or 2.

Example 5

Use of the Solutions Described Herein in a Short Lyophilization Cycle with Height of Solution in Lyophilization Vessel of 17 mm A first thrombin solution as described herein, comprising 2% mannitol, 0.6% human serum albumin, 20 mM sodium acetate (0.27%), 130 mM sodium chloride (0.76%) and 40 mM $CaCl_2$ (0.6%) in distilled water at pH 7.0; and a second solution, similar to the first solution, but comprising a sodium chloride concentration of lower than 120 mM (0.7%) sodium chloride (lower than 0.76%) were lyophilized. The first solution was lyophilized using the short lyophilization cycles described in Table 3 above; and the second solution (with the lower sodium chloride concentration) was lyophilized in a lyophilizatin cycle having a duration of 108 hours (wherein the height of each solution in the lyophilization vessel was about 17 mm).

Water content of both solid thrombin compositions, and thrombin activity recovery after reconstitution of both solid thrombin compositions were measured, as described above.

In both solid compositions, water content was 1.5% and the thrombin activity recovery was 100%.

The results show that the thrombin solution according to the invention enabled to shorten the duration of the lyophilization cycle by about 37%. In conclusion, the thrombin solution described herein advantageously enables use of a short lyophilization cycle that yields a solid composition having low water content and the high thrombin activity recovery as compared to known thrombin solutions.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

The invention claimed is:

1. A solid composition comprising thrombin, obtained by lyophilization of an aqueous thrombin solution, the method comprising:
   providing the aqueous thrombin solution comprising about 1 to less than about 4.6% w/v of a single saccharide or sugar alcohol; at least 0.7 to lower than about 1.75% w/v sodium chloride; about 0.2 to about 3% w/v albumin; calcium chloride; and sodium acetate, wherein the aqueous thrombin solution is devoid of polyethylene glycol; and lyophilizing the aqueous thrombin solution, wherein a height of the aqueous thrombin solution in a lyophilization vessel is in the range of 6 mm to 10 mm, and wherein a total lyophilization time is no greater than about 35 hours; wherein the obtained solid composition is devoid of polyethylene glycol, comprises thrombin, a single saccharide or sugar alcohol, and sodium chloride, and wherein the solid composition has a water content of less than 3%, by total weight of the composition.

2. The solid thrombin composition of claim 1, wherein the aqueous thrombin solution comprises about 200 to about 2000 IU/ml thrombin; about 0.3 to about 1.5% w/v calcium chloride; and about 0.14 to about 1% w/v sodium acetate.

3. The solid thrombin composition of claim 2, wherein the aqueous thrombin solution comprises: about 1.6 to less than about 4.6% w/v single saccharide or sugar alcohol; about 0.7 to about 1.7% w/v sodium chloride; higher than about 0.2 to lower than about 3% albumin w/v; about 0.3 to about 1.2% w/v calcium chloride; and about 0.14 to about 0.7% w/v sodium acetate.

4. The solid thrombin composition of claim 3, wherein the single saccharide or sugar alcohol is present at a concentration of 2% w/v; the albumin is present at a concentration of about 0.6% w/v; the sodium chloride is present at a concentration of about 0.76% w/v; the calcium chloride is present at a concentration of about 0.6% w/v and the sodium acetate is present at a concentration of about 0.27% w/v.

5. The solid thrombin composition of claim 1, the aqueous thrombin solution consisting essentially of thrombin; single saccharide or sugar alcohol; sodium chloride; albumin; calcium chloride; and sodium acetate.

6. The solid thrombin composition of claim 1, wherein the single sugar alcohol is mannitol.

7. The solid thrombin composition of claim 6, wherein the mannitol is present at a concentration of about 2% w/v.

8. The solid thrombin composition of claim 1, wherein the aqueous thrombin solution is devoid of histidine.

9. The solid thrombin composition of claim 1, comprising sodium chloride at an amount in the range of 6% to 45% by weight of the solid composition.

\* \* \* \* \*